United States Patent [19]

Ashihara et al.

[11] Patent Number: 4,621,048

[45] Date of Patent: Nov. 4, 1986

[54] REAGENTS CONTAINING AN ANTI-LIGAND BOUND TO AN ANTI-ENZYME AND METHODS FOR EMPLOYING SAID REAGENTS IN AN IMMUNOASSY

[75] Inventors: Yoshihiro Ashihara; Hiromasa Suzuki; Yasushi Kasahara, all of Tokyo, Japan

[73] Assignee: Fujirebio Kabushiki Kaisha, Tokyo, Japan

[21] Appl. No.: 588,682

[22] Filed: Mar. 12, 1984

[30] Foreign Application Priority Data

Mar. 11, 1983 [JP] Japan ................... 58-38975
Mar. 29, 1983 [JP] Japan ................... 58-51494
Mar. 29, 1983 [JP] Japan ................... 58-51495

[51] Int. Cl.$^4$ .......................... G01N 33/536
[52] U.S. Cl. ............................ 435/5; 435/7; 435/15; 435/17; 435/18; 435/21; 435/26; 435/188; 436/512; 436/513; 436/537; 436/548; 436/813; 436/817; 436/822; 530/389
[58] Field of Search .............. 436/501, 536, 537; 435/5, 7, 188; 436/819, 512

[56] References Cited

U.S. PATENT DOCUMENTS 4,134,792  1/1979  Boguslaski et al. .............. 435/7
4,433,059  2/1984  Chang et al. ..................... 436/512
4,446,233  5/1984  Auditore-Hargreaves et al. ............................. 436/537

FOREIGN PATENT DOCUMENTS 0088974  9/1983  European Pat. Off. ........... 435/7

Primary Examiner—Sidney Marantz
Assistant Examiner—David A. Saunders
Attorney, Agent, or Firm—Burgess, Ryan & Wayne

[57] ABSTRACT

The invention relates to a method and novel reagents for detecting a ligand in a biological sample. In the method, the sample is combined with (i) an enzyme or an enzyme bound to a first macromolecular compound, (ii) substrate for the enzyme, and (iii) an antibody complex comprising anti-ligand bound to anti-enzyme and a second macromolecular compound bound to either one or both of the anti-ligand and anti-enzyme. The activity of the enzyme varies as a function of the unknown amount of ligand contained in the biological sample.

29 Claims, No Drawings

REAGENTS CONTAINING AN ANTI-LIGAND BOUND TO AN ANTI-ENZYME AND METHODS FOR EMPLOYING SAID REAGENTS IN AN IMMUNOASSY

The present invention relates to a method of qualitatively and quantitatively measuring the presence of a ligand, for example, medicinal substances (such as drugs) and trace constituents derived from various diseases in a body fluid, such as blood serum and urine.

The analysis of such trace constituents is useful for the diagnosis of various diseases and in determining the course of treatment, and accordingly, they are utilized as clinical tests. However, these body fluids contain a variety of constituents, and some of them are similar to each other in their molecular weights, physiological activities, or molecular structures. Accordingly, such methods must be highly specific and highly sensitive to accurately determine the presence of these trace constituents. Moreover, these methods are also required to be simple, since they are often employed routinely.

Immunoassay methods utilize the high affinity between an antigen and an antibody and high specificity of an antibody which discriminates a ligand. Immunoassay methods are divided into radio-immunoassay, enzyme immunoassay, the method utilizing hemagglutination, etc.

The sensitivity of the radioimmunoassay is high. However, this method uses radioisotopes which are harmful to human beings, and accordingly, the place where the radio-immunoassay is carried out and the amount of radioisotope to be used are severely regulated, and special facilities are needed. On the other hand, such a problem does not exist in the enzyme immunoassay. However, separation of the free labelled-substance from the bound labelled-substance (a heterogeneous system) is necessary in a manner similar to the radioimmunoassay. These separation procedures are complicated, and it is a problem in its operation and results in errors in measuring. In the case of the method utilizing hemagglutination, although a separation procedure is not necessary, the sensitivity of this method is lower than the above two methods, and the determination of a very small amount of the substance to be detected, such as nanogram and picogram amounts, is difficult.

The present inventors have found that when a complex of an antibody against a ligand to be measured (anti-ligand) and an antibody against an enzyme (anti-enzyme) is reacted with the ligand to be measured and the enzyme, the enzyme activity varies according to the amount of the ligand. And, they further found that by utilizing this reaction, the ligand can easily be determined with high sensitivity.

The ligand is a substance having one or more antigenic determinant sites, and includes hormones derived from various endocrine glands such as insulin, TSH and thyroglobulin, plasma proteins such as immunoglobulin, albumin and ferritin, viral antigens such as HB antigen, bacteria, α-fetoprotein, and carcinoembryonic antigens. The ligand having a molecular weight of larger than about 100,000 daltons is preferable in certain methods of the present invention in respect of the sufficient variation of enzyme activity. However, by using a ligand bound to a macromolecular compound or a polymer of the ligand described later, lower molecular haptens may also be measured easily. Such haptens include drugs such as digoxin, theophylline, phenobarbital, phenytoin, penicillin and amikacin, and hormones such as prostaglandin, testosterone, progesterone and thyroxin.

Enzymes whose activities are easily measured are preferable. Moreover, it is necessary to obtain the antibody of the enzyme. The anti-bodies of most enzymes can easily be produced by the injection of the enzyme into the body of an animal. In the case of enzymes derived from an animal, the antibodies can also be produced by the injection into the body of other animals. Examples of such enzymes include glucose-6-phosphate dehydrogenase, hexokinase, α-amylase, malate dehydrogenase, alkaline phosphatase, peroxidase, β-galactosidase, creatine kinase, ribonuclease, and penicillinase.

In the case when an enzyme is allowed to react with the antibody complexes described later, if the enzyme activity does not appreciably vary, a macromolecular compound may preferably be bound to the enzyme prior to use. The complex of an enzyme and a macromolecular compound is termed macromolecular enzyme or an enzyme complex. Preferred macromolecular compounds are water-soluble, and their molecular weights are greater than about 100,000 daltons. Such macromolecular compounds are useful if they provide these properties in the bound state with the enzyme. For example, a lower molecular weight molecule such as bovine serum albumin is first bound to an enzyme, and thereafter the bovine serum albumin is polymerized with free bovine serum albumin molecules by self-polymerization. Examples of the macromolecular compounds include polysaccharides and their derivatives such as soluble dextran, carboxymethyl dextran, dextran containing amino groups and amylose, proteins such as gelatin, hemocyanin and ferritin, and polyethylene glycol.

Besides the enzyme, binding with the macromolecular compound may be carried out with the antibody complexes described later, or both the enzyme and the antibody complexes may be bound to the macromolecular compounds.

The binding method may be selected by considering the functional groups of both substances. Such functional groups include, amino groups, carboxyl groups, hydroxyl groups, thiol groups, imidazole groups, phenyl groups, etc. The binding of amino groups, may be carried out by many methods such as the diisocyanate method, the glutaraldehyde method, the difluorobenzene method, and the benzoquinone method, etc. As the method to bind an amino group and a carboxyl group, the peptide-binding method of carboxyl group to succinimido ester, the carbodiimide method, the Woodward reagent method are known. The periodate oxidation method (Nakane method) where a bridge between amino group and sugar chain forms is also utilized. In the case of using a thiol group, for example, a carboxyl group is first converted to a succinimido ester, and this ester group is then allowed to react with cysteine to introduce the thiol group, and both thiol groups are bound by using a thiol-reactive bifunctional cross-linking reagent such as phenylene-bismaleimide. As the method of utilizing a phenyl group, the diazotization method and the alkylation method are utilized. Other than the above, a suitable method may be selected from the various methods described in "Method in Immunology and Immunochemistry" (C. A. Williams et al., 1976, Academic Press N.Y.) and "Koso Meneki Sokutei-ho" (E. Ishikawa et al., 1978, Igaku-shoin (Japan)). The molar ratio of the combination is not limited to 1:1, and suitable ratios can be easily selected. After the binding reaction, the macromolecular enzyme produced is purified by gel filtration, ion-exchange chromatography and affinity chromatography, and lyophilized, if necessary.

The antibody against the ligand to be measured (anti-ligand) and the antibody against the enzyme (anti-enzyme) may be produced according to known methods of producing an antibody. For example, the ligand or the enzyme is injected once or several times into the subcutaneous region of the back, foot pad or femoral muscle of a warm-blooded animal, such as rabbit, goat, horse, guinea pig and chicken, in an amount of 0.3 to 2 mg per kg together with an adjuvant, and thereby the antibody is produced in the humoral fluid. These antibodies are not limited to immunoglobulins such as IgG, IgM and IgA, and include their digestion products with pepsin or papain, such as F(ab')$_2$, Fab' and Fab. As to the anti-enzyme, some antibodies entirely inhibit the enzyme activity, some antibodies partially inhibit, and some do not inhibit enzyme activity. However, any anti-enzyme can be used for the method of the invention. These antibodies are purified according to a conventional isolation method of immunoglobulin from serum, such as precipitation using ammonium sulfate, ion-exchange chromatography, gel filtration and affinity chromatography.

On the other hand, these antibodies may be produced as monoclonal antibodies. In this case, the ligand or the enzyme is injected several times into the abdominal cavity of a mouse together with an adjuvant, and its spleen is excised. The spleen cell is fused with a mouse myeloma cell by a conventional method such as by using polyethylene glycol. The hybridoma thus obtained is cultured and cloned, and the cell capable of producing the desired antibody is obtained. This cell is injected into the abdominal cavity of a mouse, and multiplied. Then, ascites are collected, and the desired antibody is separated from the ascites.

The binding method of the anti-ligand and the anti-enzyme may be selected from the binding method of mutual proteins among the binding method of the enzyme and the macromolecular compound previously described. For example, the glutaraldehyde method, the periodate oxidation method, the maleimide method, the diisocyanate method, the benzoquinone method, and the carbodiimide method are applicable. Also applicable are the SPDP method to bind an NH$_2$ group and a SH group, the method of using a lectin such as protein A which is able to bind to a sugar chain of IgG, and the rearrangement of SH groups of two kinds of F(ab')$_2$ in the presence of a reductant. The antibody complex is not limited to one where one molecule of the anti-ligand binds to one molecule of the anti-enzyme, and the same where each several molecules binds each other and the same where each molecules are polymerized, are also included. The combination ratio of each molecule is also not limited to 1:1.

As previously described, the antibody complex of an anti-ligand and anti-enzyme may also bind to the macromolecular compound. In this case, the macromolecular compound may be selected from the foregoing macromolecular compounds, and the binding method may also be selected from the foregoing methods. The binding with the macromolecular compound may be carried out against one or both of the anti-ligand and anti-enzyme prior to the binding of the antibodies, or it may also be carried out after the binding of the antibodies.

The antibody complexes bound or not bound to the macromolecular compound are purified by gel filtration, ion-exchange chromatography using a cation-exchange resin or an anion-exchange resin, and affinity chromatography, and then lyophilized, if necessary.

In order to make the variation of the enzyme activity more sensitive, a second antibody against the antibody against the ligand to be measured (hereinafter referred to as "(anti)anti-ligand") and/or a second antibody against the antibody against the enzyme (hereinafter referred to as "(anti)anti-enzyme") may preferably be employed with the combination of anti-ligand and anti-enzyme alone or combined with the macromolecular compound.

The (anti)anti-ligand and (anti)anti-enzyme are produced according to the same method previously described with respect to the anti-ligand and the anti-enzyme. These antibodies are also not limited to immunoglobulins, and include the papain or pepsin digestion products such as F(ab')$_2$, and F(ab') and Fab. And, they may be applied irrespective of their enzyme inhibitory activities. The (anti)anti-ligand and/or the (anti)anti-enzyme may also be bound to a macromolecular compound prior to use. In this case, the macromolecular compound may be selected from those previously described.

In order to make the variation of the enzyme activity more sensitive, a combination of the ligand and a macromolecular compound (hereinafter referred to as "macromolecular ligand") or a polymer comprised of the ligand as monomer units material of the same as the ligand to be measured (hereinafter referred to as "polymerized ligand") may preferably be contacted with the antibody complexes with or without the macromolecular compound. In the case of using the macromolecular ligand or the polymerized ligand, a lower molecular weight ligand, for example, having a molecular weight of less than about 100,000 is easily measured. The macromolecular compound and its binding method may be the same as previously described.

When the ligand is polymerized, the polymerization method may be selected from the binding method of the macromolecular compound previously described, and for example, it may be carried out by using a divalent cross-linking agent such as carbodiimide and glutaraldehyde.

After the reaction, the macromolecular ligand and the polymerized ligand are purified by using gel filtration, ion-exchange chromatography and affinity chromatography, and lyophilized, if necessary.

The ligand to be measured and the enzyme or the macromolecular enzyme (enzyme complex) are combined with the antibody complex with or without the macromolecular compound in an aqueous solution. The aqueous solution is preferably kept at 20° to 45° C. at pH 4 to 8.5. In order to maintain the pH constant, a buffer solution such as a phosphate buffer solution or an acetate buffer solution may be employed. The suitable amounts of the enzyme or the macromolecular enzyme and the antibody complexes are different according to the particular components chosen, the kind of the ligand to be measured and the reaction conditions, and accordingly, the relative amounts are preferably determined by a preliminary test. The reaction time of the antibody complexes with the ligand and the enzyme or the macromolecular enzyme is usually the time necessary for a sufficient reaction as for example, about 20 to 60 minutes at about 37° C. is preferable.

In the case of using the (anti)anti-ligand, the (anti)anti-enzyme, the macromolecular ligand or the polymerized ligand, one or more kinds of them may be added. Suitable amounts are determined by the variation of the enzyme activity, which is different according to the particular components chosen, and accordingly, it is preferably determined by a preliminary test. The reaction conditions may usually be the same as described above.

The order in which the antibody complex ligand, the enzyme or the macromolecular enzyme, the (anti)anti-ligand, the (anti)anti-enzyme, the macromolecular ligand and the polymerized ligand are combined is not limited, and for example, all of them may be added at the same time.

In accordance with the present method, each constituent may preferably be macromolecular having a suitable size, and in order to satisfy this requirement, for example, the macromolecular compound and the (anti)anti-ligand and (anti)anti-enzyme may preferably be employed according to the kind of the ligand, the enzyme and the antibody complexes selected. And, in the case of the macromolecular ligand and the polymerized ligand, steric hindrance is also utilized. Namely, the macromolecular ligand or the polymerized ligand and the ligand to be measured competitively react with the antibody complex, and the macromolecular ligand or the polymerized ligand bound to the antibody complex inhibits the binding of the enzyme with the antibody complex due to steric hindrance. The binding amounts of the macromolecular ligand and the polymerized ligand vary according to the amounts of the ligand to be measured, and the binding amount of the enzyme varies according to the above binding amounts.

After these reactions, the activity of the enzyme is measured and may be compared to a standard solution containing a known amount of ligand. In the method of the invention, the activity of free enzyme is different from that of the enzyme bound to the antibody complexes. Accordingly, the enzyme activity of the reaction solution containing the free enzyme and the bound enzyme is measured. The measurement is carried out according to the known method of each enzyme. For example, when glucose-6-phosphate dehydrogenase is employed, a substrate solution containing glucose-6-phosphoric acid and NADP+ is added to the reaction solution, and the yield of NADPH is determined by measuring the absorbance at 340 nm. When hexokinase is employed, a substrate solution containing glucose, ATP, NADP+ and glucose-6-phosphate dehydrogenase is added to the reaction solution, and the yield of NADPH is measured.

According to the method of the invention, a ligand can be detected and determined in high sensitivity and in high specificity. The operation of this method is simple, and a ligand can easily and inexpensively be determined.

EXAMPLE 1

(i) Preparation of Antibody Complex of Anti-Human-α-Fetoprotein Goat Fab' and Antihexokinase Guinea Pig Fab'

A goat was immunized with human α-fetoprotein (AFP) in a conventional manner, and anti-AFP goat antiserum was obtained. This antiserum was purified by using an AFP-Sepharose 4B affinity column, and dried pure anti-AFP goat specific IgG was obtained.

0.2 mg of pepsin (made by Sigma Co.) was added to 20 mg of this pure specific IgG, and digested at 37° C. overnight in 0.1M sodium acetate buffer solution of pH 4.2. The digest was adjusted to pH 7.8 by using 1N NaOH. The digest was then passed through a Sephadex G-100 column, and the fraction containing 11 mg of F(ab')$_2$ was collected by measuring the absorbance of effluent at 280 nm.

5 mg of anti-AFP goat F(ab')$_2$ was dissolved at 2 ml of 0.1M phosphate buffer solution pH 6.0 containing 1 mM EDTA, and 0.2 ml of 0.1M 2-mercaptoethylamine solution was added to this solution. The mixture solution was allowed to react at 37° C. for 90 minutes. The reaction solution was passed through a column of Sephadex G-25 (1 cm×40 cm), and gel filtration was carried out. The void fractions were collected as the anti-AFP goat Fab' fraction. 4 mg of N,N'-(1,2 phenylene)-bismaleimide was dissolved in 0.5 ml of acetone, and its volume was adjusted to 10 ml by adding 0.1M sodium acetate buffer solution pH 5.0, and 1 ml of the solution was added to the above anti-AFP goat Fab' fraction, and allowed to react at 30° C. for 20 minutes. This reaction mixture was passed through a column of Sephadex G-25 (1 cm×40 cm), and gel filtration was carried out. The void fractions were collected, and concentrated by using polyethylene glycol 20,000 at 4° C., and an antibody complex of anti-AFP goat Fab'-maleimide was obtained.

On the other hand, hexokinase (HK) was injected into a guinea pig in the conventional manner, and anti-HK guinea pig specific IgG was obtained. This specific IgG was purified by using HK-Sepharose 4B affinity column, and pure anti-HK guinea pig specific IgG was obtained. 20 mg of this pure specific IgG was treated in the same manner as the case of the foregoing anti-AFP goat specific IgG, and the fraction containing 9.8 mg of anti-HK guinea pig F(ab')$_2$ was obtaine.

In the same manner as the case of the foregoing anti-AFP goat F(ab')$_2$, 5 mg of the F(ab')$_2$ was reduced by 2-mercaptoethylamine and purified by gel filtration using Sephadex G-25 to obtain anti-HK guinea pig Fab'.

The anti-HK guinea pig Fab' thus obtained was mixed with the above antibody complex of anti-AFP goat Fab'-maleimide. The mixture was adjusted to pH 8.6 and allowed to react at 4° C. for 24 hours. The reaction mixture was concentrated by using polyethylene glycol 20,000, and gel filtration was carried out by using Sephadex G-100 column (1 cm×100 cm). The fractions corresponding to F(ab')$_2$ were collected, and 8 mg of the antibody complex of anti-AFP goat Fab'-anti-HK guinea pig Fab' was obtained.

(ii) Preparation of Macromolecular Hexokinase 50 mg of rabbit serum albumin was dissolved in 2 ml of H$_2$O, and the pH of the solution was adjusted to 6.0. 5 mg of 1-ethyl-3-(3-dimethylaminopropyl)carbodiimide hydrochloride (EDC) was added to this solution, and allowed to react at room temperature for 1 hour while the pH was kept at 6.0. The reaction mixture was centrifuged, and the supernatant was introduced into a Sephacryl S-300 column (1 cm×100 cm), and gel filtration was carried out. The void fractions were collected, and concentrated by using polyethylene glycol 20,000 to obtain the macromolecular rabbit serum albumin.

10 mg of this macromolecular rabbit serum albumin was dissolved in 1 ml of H$_2$O, and adjusted to pH 6.0. 2 mg of HK and 10 mg of EDC were added to this solution, and allowed to react at room temperature for 30 minutes while the pH was kept at 6.0. The reaction mixture was centrifuged, and the supernatant was purified by gel filtration using a Sepharose 6B column. The fractions having HK activity were collected, and the macromolecular HK was obtained.

(iii) Measurement of Human α-Fetoprotein 10 ug/ml AFP was diluted twice by twice, and each 10 ul of 2n dilution series was prepared. Each 20 ul of 20 mM phosphate buffered saline solution pH 7.0 containing 40 ug of the antibody complex of anti-AFP goat Fab'-anti-HK guinea pig Fab' was added to each diluted solution, and each 20 ul of the macromolecular HK solution having a relative activity ($\Delta OD_{340\ nm}$/minute) of 0.06 was further added. The mixture was allowed to stand at room temperature for 30 minutes.

Each 1 ml of 50 mM tris-HCl buffer solution pH 8.0 containing 0.1M D-glucose, 0.5 mM ATP, 0.2 mM NADP, 13.3 mM $MgCl_2$ and 3 IU/ml G6PDH was added to the mixture as substrate, and mixed well. Then, the variation of the absorbance at 340 nm was measured, and the following results were obtained.

TABLE 1

| AFP (ng) | ($\Delta OD_{340nm}$/min) × 1000 |
|---|---|
| 0 | 20.0 |
| 68 | 17.5 |
| 135 | 16.3 |
| 270 | 15.2 |
| 540 | 12.4 |
| 1080 | 10.5 |

As to 5 human serum samples, the same measurements were carried out by using each 50 ul serum, and AFP concentration of each sample was determined by using the results of Table 1 as a calibration curve. On the other hand, AFP concentrations of the same sera were also measured by radioimmunoassay (RIA).

The results are shown in Table 2.

TABLE 2

| | AFP | |
|---|---|---|
| Serum | The Method of the Invention | RIA Method |
| A1 | 200 ng | 192 ng |
| A2 | 523 | 545 |
| A3 | 421 | 401 |
| A4 | 823 | 811 |
| A5 | 495 | 502 |

EXAMPLE 2

(i) Preparation of Antibody complex of Anti-Human IgG (Guinea Pig IgG fraction) and Anti-glucose-6-Phosphate Dehydrogenase Guinea Pig IgG 5 mg of anti-human IgG (guinea pig IgG fraction) (α-hIgG) was dissolved in 1 ml of 0.1M phosphate buffer solution pH 6.3, and 100 ul of 2 mg/ml 4-maleimidomethyl-cyclohexane-1-carboxylic acid succinimide ester (CHMS) dioxane solution was added to this solution. The mixture was allowed to stand at room temperature for 1 hour. This mixture was placed in a Sephadex G-25 column (1 cm×50 cm) and gel filtration was carried out by using 0.1M phosphate buffer solution having a pH of 6.5 containing 1 mM EDTA to remove unreacted CHMS. The solution of the antibody complex of 4-maleimidomethylcyclohexane-1-carboxylic acid and α-hIgG (CHM induced α-hIgG) thus obtained was concentrated to 1 ml.

5 mg of anti-glucose-6-phosphate dehydrogenase guinea pig IgG (α-G6PDHIgG) was dissolved in 0.1M phosphate buffer solution having a pH of 7.5 containing 5 mM EDTA, and 100 ul of 9 mg/ml S-acetylmercaptosuccinic anhydride dimethyl sulfoxide solution was added, and allowed to warm at 37° C. for 1 hour. Subsequently, 110 ul of 1M hydroxylamine solution having a pH of 7.5 was added, and allowed to react at 37° C. for 30 minutes. The reaction mixture was placed in Sephadex G-25 column, and gel filtration was carried out by using 0.1M phosphate buffer solution (pH 6.5) containing 1 mM EDTA to remove unreacted S-acetylmercaptosuccinic acid.

The SH induced α-G6PHDIgG thus obtained was concentrated to 1 ml, and 1 ml of the concentrated CHM induced α-hIgG solution previously described was added. The mixture was allowed to react at 4° C. overnight, and the reaction mixture was purified by gel filtration using Sephacryl S-300 (1 cm×120 cm) to obtain the antibody complex of α-hIgG and α-G6PDHIgG having a molar ratio of 1:1.

(ii) Preparation of Macromolecular Antibody Complex

The above combination matter was dialyzed against pH 8.0 of 0.1M carbonate buffer solution the protein concentration of the dialyzate was adjusted to 5 mg/ml, and 20 mg of succinimide ester of carboxydextran (MW=$10^7$) which was previously prepared was added, and stirred at 37° C. for 2 hours.

Subsequently, the reaction mixture was treated by gel filtration using Sepharose 4B, and void fractions were collected. The fractions were concentrated, and the desired α-hIgG-α-G6PDHIgG-dextran Antibody complex (G-H-D antibody complex) was obtained.

(iii) Measurement of Human IgG

Each 50 ul of the G-H-D antibody complex was added to each 50 ul of human IgG solution having various concentrations, and allowed to warm at 37° C. for 1 hour. 100 ul of glucose-6-phosphate dehydrogenase (G6PDH) was added to the mixture, and allowed to react at 37° C. for 20 minutes. 1.0 ml of a substrate solution (pH 8.5) containing 0.5 mM glucose-6-phosphoric acid, 1.3 mM NADP, 0.1M glycylglycine and 20 mM $MgCl_2$ was added to the reaction mixture, and an increasing rate of absorbance at 340 nm at 30° C. was measured. The results are shown in Table 3.

TABLE 3

| Human IgG (ug) | ($\Delta OD_{340nm}$/min) |
|---|---|
| 0 | 0.080 |
| 5 | 0.070 |
| 25 | 0.062 |
| 50 | 0.050 |
| 200 | 0.035 |
| 800 | 0.028 |

As to 4 serum samples, the same measurements were carried out by using each 50 ul serum, and IgG concentration of each sample was determined by using the results of Table 3 as a calibration curve. On the other hand, IgG concentrations of the same sera were also measured by the conventional SRID method.

The results are shown in Table 4.

TABLE 4

| Serum | IgG Concentration | |
|---|---|---|
| | The Method of the Invention | SRID Method |
| B1 | 12.2 mg/ml | 11.8 mg/ml |
| B2 | 11.8 | 12.0 |
| B3 | 8.9 | 8.2 |
| B4 | 14.3 | 13.5 |

EXAMPLE 3

(i) Preparation of Antibody complex of Anti-Human IgG (Guinea Pig IgG and Antihexokinase Guinea Pig IgG fraction)

Except for employing antihexokinase guinea pig IgG ($\alpha$-HKIgG) instead of the $\alpha$-G6PDHIgG, the preparation was carried out in the same manner as item (i) of Example 2, and the fraction containing 4 mg of the antibody complex of $\alpha$-hIgG and $\alpha$-HKIgG was obtained.

(ii) Measurement of Human IgG

Each 50 ul of the above antibody complex of $\alpha$-HIgG$\alpha$-HKIgG was added to each 50 ul of human IgG solution having various concentrations. Each 100 ul of 1/100 diluted solution of $\alpha$-guinea pig IgG-IgG serum was added to the mixture, and allowed to warm at 25° C. for 1 hour. Then, 25 ul of the solution containing 0.4 ug of hexokinase was added, and allowed to react at 25° C. for 30 minutes. 3 ml of 50 mM tris buffer solution of pH 8.0 containing 0.1M glucose, 0.5 mM ATP, 0.2 mM NADP, 3 U/ml glucose-6-phosphate dehydrogenase, and 13.3 mM MgCl$_2$ was added as substrate, and an increasing rate of absorbance at 340 nm at 25° C. was measured. The results are shown in Table 5.

TABLE 5

| Human IgG | ($\Delta OD_{340nm}$/min) $\times$ 1000 |
|---|---|
| 0.6 ug/ml | 19.5 |
| 2.0 | 17.0 |
| 5.0 | 14.1 |
| 20.0 | 11.3 |
| 100 | 8.5 |

As to five human serum samples, the same measurements were carried out by using each 50 ul of 1000 times diluted serum, and the IgG concentration of each sample was determined by using the results of Table 5 as a calibration curve. On the other hand, the IgG concentration of the same sera were also measured by the conventional SRID method.

The results are shown in Table 6.

TABLE 6

| Serum | IgG Concentration | |
|---|---|---|
| | The Method of the Invention | SRID Method |
| C1 | 8.4 mg/ml | 9.1 mg/ml |
| C2 | 16.1 | 17.2 |
| C3 | 11.5 | 10.3 |
| C4 | 12.1 | 11.8 |
| C5 | 7.5 | 8.1 |

EXAMPLE 4

(i) Preparation of Anti-Glucose-6-Phosphate Dehydrogenase Mouse IgG

As an antigen, G6PDP derived from an yeast (manufactured by Oriental Yeast Co., Ltd.) was employed. 1 mg/ml of this G6PDH solution was mixed with the equal volume of Freund complete adjuvant to form an emulsion, and 0.1 ml of this emulsion was injected three times into the abdominal cavity of a BALB/C mouse of 8 weeks growth every two weeks. After a week, 50 ug/0.1 ml of G6PDH solution was injected into the mouse tail vein, and 3 days later, the spleen was excised. This spleen was ground, and a spleen cell was separated. The spleen cell was fused with mouse myeloma P3U1 cell by using polyethylene glycol 1500.

The hybridoma was placed in each well of a plate having 96 wells, and cultured in the HAT medium. The cell of each well was examined by the ELISA method using a plate where G6PDH was immobilized, and 5 wells containing the mouse IgG being specific to G6PDH were found. The cells of these 5 wells were diluted by the limit dilution method and cloned, and two cell lines recognizing different ligands of G6PDH were obtained by examining the method of inhibition test by the ELISA method.

Each cell line was multiplied in 10% FCS-RPMI medium, and each 10$^7$ of the multiplied cells were injected into the abdominal cavity of a BALB/C mouse into which pristane was previously injected. After two weeks, about 10 ml of ascites were withdrawn. The ascites were treated by the precipitation method using ammonium sulfate in 45% saturation, and the precipitates were separated. The precipitates were dissolved in a small amount of a phosphate buffer solution of pH 7.0, and separated by gel filtration using Sephacryl S-300 column which was previously equilibrated with the same buffer solution and the IgG fractions were collected.

Equal amounts of two IgG recognizing different ligands thus obtained were mixed with each other, and used as the anti-glucose-6-phosphate dehydrogenase mouse IgG.

(ii) Preparation of Human $\alpha$-Fetoprotein Mouse IgG

In to the same manner as above, two kinds of mouse monoclonal antibodies against AFP were prepared. Each antibody was purified to obtain IgG, and they were mixed with each other and used as human $\alpha$-fetoprotein mouse IgG ($\alpha$-AFP IgG).

(iii) Preparation of Antibody complex of $\alpha$-AFPIgG and $\alpha$-G6PDHIgG 50 mg of dextran T500 (mean molecular weight: 500,000 manufactured by Pharmacia Fine Chemicals) was dissolved in 1 ml of water, and 0.2 ml of 0.1M sodium periodate was added. Then, the mixed solution was allowed to react at 4° C. overnight. 0.15 ml of ethylene glycol was added to the reaction mixture, and allowed to react for 5 minutes. Subsequently, the reaction mixture was treated by gel filtration using Sephadex G-25 column which was previously equilibrated with 1 mM sodium acetate buffer solution of pH 5.0, and void fractions were collected. The solution of 20 mg of the mixture of $\alpha$-AFPIgG and $\alpha$-G6PDHIgG dissolved in 10 mM carbonate buffer solution of pH 9.5 was added to the fractions, and pH of this mixed solution was adjusted to 9.5. This mixed solution was then allowed to react at room temperature for 2 hours. Then, 0.5 ml of 0.4% sodium borohydride was added to this solution, and further allowed to react at 4° C. for 2 hours. This reaction mixture was dialyzed against 20 mM phosphate buffer solution pH 7.0. The dialyzate was separated by gel filtration using a Sephacryl S-300 column, and the fractions of the antibody complex of α-AFPIgG and α-G6PDHIgG were collected.

(iv) Measurement of AFP

Each 50 ul of the above fractions of the antibody complex of α-AFPIgG and α-G6PDHIgG was added to each 50 ul of AFP having various concentrations. Each 100 ul of rabbit anti mouse IgG-IgG fractions containing G6PDH was added to the mixture, and allowed to react at 25° C. for 30 minutes. 1.0 ml of 0.1M glycylglycine buffer solution (pH 8.5) containing 0.5 mM glucose-6-phosphate, 0.5 mM NADP and 20 mM $MgCl_2$ was added as the substrate for G6PDH, and an increasing rate of absorbance at 340 nm at 25° C. was measured. The results are shown in Table 7.

TABLE 7

| AFP | ($\Delta OD_{340nm}$/min) × 1000 |
|---|---|
| 0 ng | 36.5 |
| 50 | 28.1 |
| 100 | 22.3 |
| 200 | 19.8 |
| 400 | 16.9 |
| 800 | 15.1 |

As to five human serum samples, the same measurements were carried out by using each 50 ul of the sample serum, and AFP concentration of each sample was determined by using the results of Table 7 as a calibration curve. On the other hand, the AFP concentration of the same sera were also measured by the conventional RIA method.

The results are shown in Table 8.

TABLE 8

| | AFP Concentration | |
|---|---|---|
| Serum | The Method of the Invention | RIA Method |
| D1 | 200 ng | 187 |
| D2 | 60 | 53 |
| D3 | 320 | 334 |
| D4 | 530 | 551 |
| D5 | 105 | 112 |

EXAMPLE 5

(i) Preparation of the Combination of Theophylline and Dextran 1 g of dextran having a molecular weight of about 2,000,000 was suspended in 50 ml of 1N sodium hydroxide 90% ethanol solution. 1 g of chloroacetic acid was added to this solution, and stirred at 37° C. for 16 hours. The precipitates were collected by filtration, washed sufficiently with ethanol, and dissolved in water. This aqueous solution was introduced into a column packed with Sephadex G-25, and unreacted chloroacetic acid was removed. The carboxymethyl dextran fractions which are void fractions were collected, and lyophilized.

500 mg of this carboxymethyl dextran was suspended in dioxane, and 500 mg of N-hydroxysuccinimide and 500 mg of soluble carbodiimide was added. The mixture was stirred overnight at room temperature. The precipitates were collected by a glass filter and washed sufficiently with dioxane and then with ether. The washed precipitates were dried to obtain succinimide ester of carboxymethyl dextran.

200 mg of this carboxymethyl dextran succinimide ester was added to 0.1M hexamethylenediamine solution (pH 8.0), and stirred at room temperature for 2 hours. Subsequently, gel filtration was carried out by using a column of Sephadex G-25, and void fractions were collected. The fractions were lyophilzed, and the lyophilized matter of the dextran induced amino group was obtained.

10 mg of 3-carboxytheophylline and 100 mg of the above dextran induced amino group were dissolved in water, and pH of the solution was adjusted to 6.0. 20 mg of soluble carbodiimide was added to the solution, and allowed to react for 1 hour while the pH was maintained at 6.0. The reaction mixture was introduced into a column of Sephadex G-25 which was previously equilibrated with 20 mM phosphate buffered saline solution pH 7.0, and gel filtration was carried out. Void fractions were collected and lyophilized to obtain the desired combination of theophylline and dextran.

(ii) Preparation of Antibody complex of Antitheophylline Rabbit Antibody and Anti-G6PDH Mouse Monoclonal Antibody Except for employing antitheophylline rabbit IgG and anti-G6PDH mouse monoclonal antibody (anti-G6PDH and antibody) instead of α-hIgG and α-G6PDHIgG, the preparation was carried out in the same manner as item i) of Example 2, and the fraction containing the antibody complex of antitheophylline rabbit antibody and anti-G6PDH antibody of which molar ratio was 1:1 was obtained.

(iii) Measurement of Theophylline

Each 50 ul of the solution containing 30 ug of the combination of theophylline and dextran and 100 ug of the above antibody complex was added to each 50 ul of theophylline solution having various concentrations, and allowed to warm at 37° C. for 30 minutes. Then, 50 ul of the solution containing 1 ug of G6PDH was added to the mixed solution, and after 30 minutes, 1.0 ml of 0.1M glycylglycine buffer solution (pH 8.5) containing 0.5 mM glucose-6-phosphoric acid, 0.5 mM NADP and 20 mM $MgCl_2$ was added, and an increasing rate of absorbance at 340 nm at 30° C. was measured. The results are shown in Table 9.

TABLE 9

| Theophylline | ($\Delta OD_{340nm}$/min) |
|---|---|
| 0 ug | 0.091 |
| 2.0 | 0.081 |
| 5.0 | 0.072 |
| 10.0 | 0.054 |
| 20.0 | 0.032 |
| 30.0 | 0.026 |
| 40.0 | 0.024 |

As to five human serum samples, the same measurements were carried out by using each 50 ul of the sample serum, and theophylline concentration of each sample was determined by using the results of Table 9 as a calibration curve. On the other hand, theophylline concentration of the same sera were also measured by the conventional RIA method.

The results are shown in Table 10.

TABLE 10

| | Theophylline Concentration | |
|---|---|---|
| Serum | The Method of the Invention | RIA Method |
| E1 | 0.5 ug/ml | 0.31 ug/ml |

TABLE 10-continued

| Serum | Theophylline Concentration | |
| --- | --- | --- |
| | The Method of the Invention | RIA Method |
| E2 | 2.0 | 2.6 |
| E3 | 15.0 | 14.6 |
| E4 | 13.1 | 13.3 |
| E5 | 10.6 | 10.1 |

EXAMPLE 6

(i) Preparation of Anti-Human IgG Goat IgG F(ab')$_2$ 10 mg of anti-human IgG goat IgG was dissolved in 2 ml of 0.1M sodium acetate (pH 4.2), and 100 ug of pepsin was added to the solution and stirred at 37° C. overnight. The pH of this digest solution was adjusted to 7.5, and gel filtration was carried out by using Sephadex G-100. The fractions of molecular weight of about 100,000 were collected, and concentrated by using polyethylene glycol to obtain the anti-human igG goat IgG F(ab')$_2$ (containing 6 mg of protein).

(ii) Preparation of Anti-G6PDH Mouse IgG Fab 10 mg of anti G6PDH mouse IgG was treated in the same manner as above, and 3.6 mg of anti-G6PDH mouse IgG Fab was obtained.

(iii) Preparation of Macromolecular Human IgG 5 mg of human IgG was dissolved in 1 ml of 10 mM phosphate buffer solution (pH 6.0), and 10 mg of soluble carbodiimide was added. This solution was kept at pH 6.0 by using 0.1N NaOH and 0.1N HCl, and when the solution became somewhat turbid, the solution was passed through a column of Sephadex G-25 which was previously equilibrated with 20 mM phosphate buffer solution pH 7.0 and desalted. Void fractions were collected, and further treated by gel filtration using Sepharose 4B, and void fractions were collected to obtain the macromolecular human IgG.

(iv) Preparation of Antibody complex of Anti-Human IgG Goat IgG Fab and Anti-G6PDH Mouse IgG Fab 2 mg of anti-G6PDH mouse IgG Fab was dissolved in 1 ml of 0.1M phosphate buffer solution (pH 6.0), and 100 ul of 2.0 mg/ml CHMS acetone solution was added, and allowed to react at 30° C. for 90 minutes. This reaction mixture was introduced into a Sephadex G-25 column which was previously equilibrated with 0.1M phosphate buffer solution (pH 6.3), and gel filtration was carried out. Void fractions were collected, and concentrated to 1 ml to obtain 2 mg of CHM induced anti-G6PDH mouse IgG Fab.

Next, 1 mg of anti-human IgG goat IgG F(ab')$_2$ was dissolved in 0.1M phosphate buffer solution (pH 6.0), and 100 ul of 56 mg/ml distilled water of 2-mercaptoethylamine solution was added. The mixed solution was allowed to react at 37° C. for 1.5 hours. The reaction mixture was treated by gel filtration using Sephadex G-25 which was previously equilibrated by 0.1M phosphate buffer solution (pH 6.3) containing 1 mM EDTA. Void fractions were collected, and concentrated to 1 ml by using polyethylene glycol.

This concentrate was mixed with the above CHM induced anti-G6PDH mouse IgG Fab solution, and allowed to stand overnight. Subsequently, gel filtration was carried out by using Sephadex G-150 which was previously equilibrated with 20 mM phosphate buffered saline solution (pH 7.0), and the fractions of molecular weight of about 100,000 were collected. The fractions were concentrated to 2 ml, and the object antibody complex was obtained.

(v) Measurement of Human IgG 50 ul of the solution containing 1.0 mg of the macromolecular human IgG was placed in a small test tube, and the solution containing human IgG of which concentration is described in Table 11 and 50 ul of the above concentrate of the antibody complex of anti-G6PDH mouse IgG Fab and anti-human IgG goat IgG Fab were added. The mixed solution was allowed to stand at 37° C. for 30 minutes. 50 ul of the solution containing 1 ug of G6PDH was added to this, and allowed to stand at 37° C. for 30 minutes. Subsequently, 1.0 ml of the substrate solution (pH 8.5) containing 0.5 mM glucose-6-phosphoric acid, 0.15 mM NADP$^+$, 20 mM MgCl$_2$ and 0.1M glycylglycine, and an increasing rate of absorbance at 340 nm was measured. The results are shown in Table 11.

TABLE 11

| Human IgG | ($\Delta OD_{340nm}$/min) |
| --- | --- |
| 0 ug | 0.090 |
| 100 | 0.080 |
| 300 | 0.062 |
| 600 | 0.041 |
| 1200 | 0.032 |
| 2500 | 0.025 |

As to five human serum samples, the same measurements were carried out by using each 50 ul serum, and IgG concentration of each sample was determined by using the results of Table 11 as a calibration curve. On the other hand, IgG concentrations of the same sera were also measured by the conventional SRID method. The results are shown in Table 12.

TABLE 12

| Serum | IgG Concentration | |
| --- | --- | --- |
| | The Method of the Invention | SRID Method |
| F1 | 11.2 mg/ml | 10.9 mg/ml |
| F2 | 8.6 | 9.1 |
| F3 | 13.5 | 12.1 |
| F4 | 13.7 | 13.6 |
| F5 | 12.2 | 11.8 |

What is claimed is:

1. A method of detecting the presence of a ligand in a biological sample suspected of containing said ligand comprising:
   (a) combining in a buffered solution said biological sample; an enzyme or enzyme complex, said enzyme complex comprising an enzyme bound to a first macromolecular compound; a substrate for said enzyme; and an antibody complex, said antibody complex comprising anti-ligand bound to anti-enzyme and a second macromolecular compound bound to at least one of said anti-ligand and said anti-enzyme;
   (b) measuring the activity of said enzyme or enzyme complex in said buffered solution; and
   (c) comparing the activity of said enzyme or enzyme complex in said buffered solution with the enzyme activity of a standard solution containing a known amount of said ligand.

2. The method of claim 1 wherein the enzyme is selected from the group consisting of glucose-6-phosphate dehydrogenase, hexokinase, α-amylase, malate dehydrogenase, alkaline phosphatase, peroxidase, β-galactosidase, creatine kinase, ribonuclease, and penicillinase.

3. The method of claim 1 wherein at least one of said anti-ligand and said anti-enzyme is a monoclonal antibody.

4. The method of claim 1 wherein said anti-ligand and said anti-enzyme are selected from the group consisting of IgG, IgM, IgA, F(ab')$_2$, Fab' and Fab.

5. The method of claim 1, wherein said second macromolecular compound is bound to both of said anti-ligand and said anti-enzyme.

6. The method of claim 1 wherein the ligand has a molecular weight of at least about 100,000 daltons.

7. The method of claim 6 wherein the ligand is selected from the group consisting of a hormone derived from an endocrine gland, a plasma protein, a viral antigen, a bacterium, and a carcinoembryonic antigen.

8. The method of claim 1 wherein the ratio of said anti-ligand to said anti-enzyme is 1:1.

9. The method of claim 1 wherein the reaction is conducted for about 20 to 60 minutes at a temperature of between about 20° and 45° C.

10. The method of claim 9 wherein the temperature is 37° C.

11. The method of claim 1 wherein said first or second macromolecular compound is water-soluble and has a molecular weight of at least about 100,000 daltons.

12. The method of claim 11 wherein said first or second macromolecular compound is selected from the group consisting of polysaccharides, derivatives of polysaccharides, proteins, and polyethylene glycol.

13. The method of claim 12 wherein said polysaccharides or derivatives of polysaccharides are selected from the group consisting of soluble dextran, carboxymethyl dextran, dextran containing amino groups and amylose.

14. The method of claim 3 wherein said protein is selected from the group consisting of gelatin, hemocyanin and ferritin.

15. The method of claim 1, wherein said antibody complex further comprises at least one member selected from the group consisting of (anti)anti-ligand, (anti)anti-ligand bound to said second macromolecular compound, (anti)anti-enzyme and (anti)anti-enzyme bound to said second macromolecular compound.

16. The method of claim 15 wherein the enzyme is selected from the group consisting of glucose-6-phosphate dehydrogenase, hexokinase, α-amylase, malate dehydrogenase, alkaline phosphatase, peroxidase, β-galactosidase, creatine kinase, ribonuclease, and penicillinase.

17. The method of claim 15 wherein at least one of said anti-ligand and said anti-enzyme is a monoclonal antibody.

18. The method of claim 15 wherein said anti-ligand and said anti-enzyme are selected from the group consisting of IgG, IgM, IgA, F(ab')$_2$, Fab' and Fab.

19. The method of claim 15 wherein the ligand has a molecular weight of at least about 100,000 daltons.

20. The method of claim 19 wherein the ligand is selected from the group consisting of a hormone derived from an endocrine gland, a plasma protein, a viral antigen, a bacterium, and a carcinoembryonic antigen.

21. The method of claim 15 wherein said second macromolecular compound is water-soluble and has a molecular weight of at least about 100,000 daltons.

22. The method of claim 21 wherein said second macromolecular compound is selected from the group consisting of polysaccharides, derivatives of poysaccharides, proteins, and polyethylene glycol.

23. The method of claim 19, wherein said ligand has a molecular weight of less than about 100,000 daltons.

24. The method of claim 23, wherein said ligand is a hapten.

25. The method of claim 24, wherein said hapten is selected from the group consisting of drugs and hormones.

26. A reagent for use in an immunoassay method for the detection of a ligand in a biological sample comprising:
an anti-ligand bound to anti-enzyme and a first macromolecular compound bound to at least one of said anti-ligand and said anti-enzyme.

27. The reagent of claim 26 further comprising at least one member selected from the group consisting of (anti)anti-ligand, (anti)anti-ligand bound to a said first macromolecular compound, (anti)anti-enzyme and (anti)anti-enzyme bound to a said first macromolecular compound.

28. The reagent of claim 26 further comprising at least one member selected from the group consisting of (i) a polymer comprised of said ligand as monomer units and (ii) said ligand bound to a second macromolecular compound.

29. The reagent of claim 28 further comprising at least one member selected from the group consisting of (anti)anti-ligand, (anti)anti-ligand bound to a said first macromolecular compound, (anti)anti-enzyme and (anti)anti-enzyme bound to a said first macromolecular compound.

* * * * *